(12) United States Patent
Moskowitz et al.

(10) Patent No.: US 10,688,486 B2
(45) Date of Patent: Jun. 23, 2020

(54) SYSTEMS AND METHODS FOR CONTROLLING EXCESSIVE FLUID FLOW IN A CASSETTE DESIGNED TO RECEIVE A FLUID SAMPLE

(71) Applicant: Polymer Technology Systems, Inc., Indianapolis, IN (US)

(72) Inventors: Keith Moskowitz, Indianapolis, IN (US); Christopher Dailey, Indianapolis, IN (US); Charles Xie, Indianapolis, IN (US); Richard Lee, Indianapolis, IN (US); Bao Phan, Indianapolis, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 388 days.

(21) Appl. No.: 15/256,030

(22) Filed: Sep. 2, 2016

(65) Prior Publication Data

US 2017/0056876 A1    Mar. 2, 2017

Related U.S. Application Data

(60) Provisional application No. 62/213,469, filed on Sep. 2, 2015.

(51) Int. Cl.
*B01L 3/00* (2006.01)
*A61B 5/15* (2006.01)
(Continued)

(52) U.S. Cl.
CPC ...... *B01L 3/5023* (2013.01); *A61B 5/150022* (2013.01); *A61B 5/150358* (2013.01);
(Continued)

(58) Field of Classification Search
CPC .......... B01L 3/5023; B01L 2200/0621; B01L 2200/026; B01L 2300/069;
(Continued)

(56) References Cited

U.S. PATENT DOCUMENTS

| 2010/0226822 A1 | 9/2010 | Ramel |
| 2012/0076693 A1 | 3/2012 | Hopper |

(Continued)

FOREIGN PATENT DOCUMENTS

WO    WO 00/19955 A1    4/2000

OTHER PUBLICATIONS

International Search Report and Written Opinion dated Nov. 28, 2016 for PCT/US2016/050200.

*Primary Examiner* — Samuel P Siefke
(74) *Attorney, Agent, or Firm* — Haynes and Boone, LLP

(57) ABSTRACT

A pinch wall and dam system for controlling fluid flow movement between a sample receiving pad and a test strip includes a sample receiving pad and a test strip in contact with the sample receiving pad. The fluid seeps more quickly under the first portion of the pinch wall than under the second portion of the pinch wall, such that the test strip becomes saturated prior to excess fluid being absorbed in the portion of the sample receiving pad away from the test strip such that the test strip does not become flooded, the portion of the sample receiving pad positioned away from the test strip being sufficiently sized to absorb the excess fluid. The pinch wall and dam system further includes a dam, sitting on top of the sample receiving pad, the dam preventing the backflow of fluid from an area near the first portion of the pinch wall.

16 Claims, 4 Drawing Sheets

(51) Int. Cl.
*G01N 33/487* (2006.01)
*G01N 35/00* (2006.01)

(52) U.S. Cl.
CPC .... *G01N 33/4875* (2013.01); *B01L 2200/026* (2013.01); *B01L 2200/0621* (2013.01); *B01L 2300/069* (2013.01); *B01L 2300/0825* (2013.01); *B01L 2300/0864* (2013.01); *B01L 2400/0406* (2013.01); *B01L 2400/0481* (2013.01); *G01N 2035/00128* (2013.01)

(58) Field of Classification Search
CPC ..... B01L 2300/0864; B01L 2400/0406; B01L 2400/0481; B01L 2300/0825; A61B 5/150022; A61B 5/150358; G01N 33/4875; G01N 2035/00128
See application file for complete search history.

(56) References Cited

U.S. PATENT DOCUMENTS

| | | |
|---|---|---|
| 2014/0199710 A1 | 7/2014 | Sambursky |
| 2015/0105300 A1 | 4/2015 | Chen |

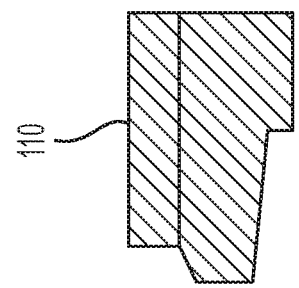
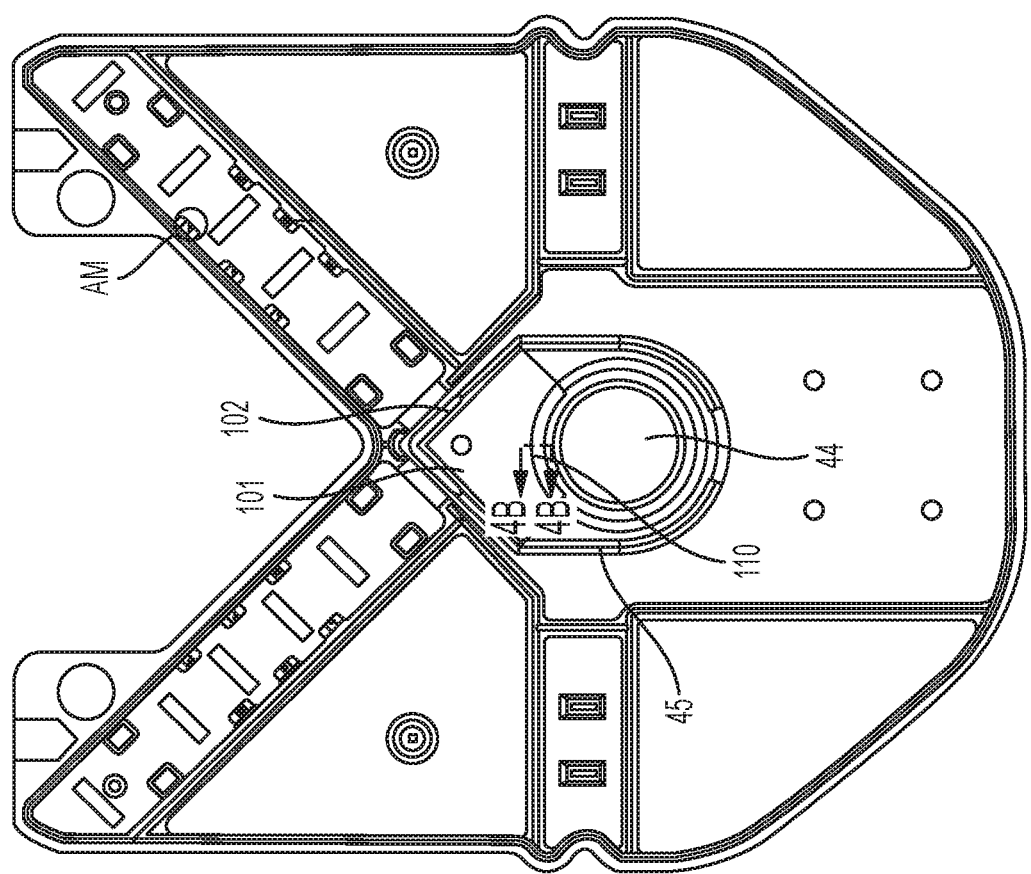

SYSTEMS AND METHODS FOR CONTROLLING EXCESSIVE FLUID FLOW IN A CASSETTE DESIGNED TO RECEIVE A FLUID SAMPLE

CROSS REFERENCE TO RELATED APPLICATIONS

This application claims the benefit of U.S. Provisional Application No. 62/213,469, filed on Sep. 2, 2015, which is incorporated herein by reference in its entirety

BACKGROUND

Blood testing for analytes, diseases, infections, and other conditions that may be detected via blood analysis is a useful diagnostic tool. Point-of-care analysis of blood for analytes is very useful and appealing to medical personnel. Such tests, if designed to detect certain analytes, may function better when a premixing set is used. Additionally, when the sample is applied to a cassette containing a test strip, the flow of the sample is important as it affects the accuracy and precision of the test. Therefore, a system with sample flow controls that can receive a sampler is desirable.

BRIEF SUMMARY

In one embodiment, a pinch wall and dam system for controlling fluid flow movement between a sample receiving pad and a test strip includes a sample receiving pad and a test strip in contact with the sample receiving pad. The pinch wall and dam system further include a pinch wall sitting on top of the sample receiving pad, the pinch wall compressing the sample receiving pad, the pinch wall comprising: a first portion separating a sample receiving portion of the sample receiving pad from a portion of the sample receiving pad positioned adjacent to the test strip, and a second portion separating the sample receiving portion of the sample receiving pad from a portion of the sample receiving pad positioned away from the test strip. The portion of the sample receiving pad that receives the sample thereon is positioned on an opposite side of the pinch wall from the portion of the sample receiving pad positioned away from the test strip. The first portion of the pinch wall compresses the sample receiving pad to a lesser degree than the second portion of the pinch wall. The fluid seeps more quickly under the first portion of the pinch wall than under the second portion of the pinch wall, such that the test strip becomes saturated prior to excess fluid being absorbed in the portion of the sample receiving pad away from the test strip such that the test strip does not become flooded, the portion of the sample receiving pad positioned away from the test strip being sufficiently sized to absorb the excess fluid. The pinch wall and dam system further include a dam, sitting on top of the sample receiving pad, the dam preventing the backflow of fluid from an area near the first portion of the pinch wall. Optionally, the first and second portions of the pinch wall together continuously surround the sample receiving portion of the sample receiving pad. Alternatively, the pinch wall compresses the sample receiving pad such that fluid received onto the sample receiving pad preferentially tends to flow from the sample receiving portion of the sample receiving pad into the portion of the sample receiving pad positioned adjacent to the test strip, and less so from the sample receiving portion of the sample receiving pad to the portion of the sample receiving pad positioned away from the test strip. In one configuration, the sample receiving pad is in a case with a cartridge with a top portion and a bottom portion, and the pinch wall and dam protrude from the top portion. In another configuration, the dam compresses the receiving pad. Optionally, the dam does not significantly compress the receiving pad, but forms a barrier against backflow. Alternatively, the top portion includes a hole for receiving a sample, wherein the dam is oriented on an edge of the hole. In one alternative, the edge of the hole is a portion of the hole proximate to the first portion of the pinch wall.

In one embodiment, a method of controlling fluid flow movement between a sample receiving pad and a test strip includes providing a pinch wall and dam system. The pinch wall and dam system include a sample receiving pad and a test strip in contact with the sample receiving pad. The pinch wall and dam system further include a pinch wall sitting on top of the sample receiving pad, the pinch wall compressing the sample receiving pad, the pinch wall comprising: a first portion separating a sample receiving portion of the sample receiving pad from a portion of the sample receiving pad positioned adjacent to the test strip, and a second portion separating the sample receiving portion of the sample receiving pad from a portion of the sample receiving pad positioned away from the test strip. The portion of the sample receiving pad that receives the sample thereon is positioned on an opposite side of the pinch wall from the portion of the sample receiving pad positioned away from the test strip. The first portion of the pinch wall compresses the sample receiving pad to a lesser degree than the second portion of the pinch wall. The fluid seeps more quickly under the first portion of the pinch wall than under the second portion of the pinch wall, such that the test strip becomes saturated prior to excess fluid being absorbed in the portion of the sample receiving pad away from the test strip such that the test strip does not become flooded, the portion of the sample receiving pad positioned away from the test strip being sufficiently sized to absorb the excess fluid. The pinch wall and dam system further include a dam, sitting on top of the sample receiving pad, the dam preventing the backflow of fluid from an area near the first portion of the pinch wall. The method further includes placing a sample on the sample receiving pad. The method further includes flowing the sample to the test strip via the first portion of the pinch wall and preventing backflow of the sample with the dam. Optionally, the first and second portions of the pinch wall together continuously surround the sample receiving portion of the sample receiving pad. Alternatively, the pinch wall compresses the sample receiving pad such that fluid received onto the sample receiving pad preferentially tends to flow from the sample receiving portion of the sample receiving pad into the portion of the sample receiving pad positioned adjacent to the test strip, and less so from the sample receiving portion of the sample receiving pad to the portion of the sample receiving pad positioned away from the test strip. In one configuration, the sample receiving pad is in a case with a cartridge with a top portion and a bottom portion, and the pinch wall and dam protrude from the top portion. In another configuration, the dam compresses the receiving pad. Optionally, the dam does not significantly compress the receiving pad, but forms a barrier against backflow. Alternatively, the top portion includes a hole for receiving a sample, wherein the dam is oriented on an edge of the hole. In one alternative, the edge of the hole is a portion of the hole proximate to the first portion of the pinch wall.

BRIEF DESCRIPTION OF THE DRAWINGS

FIGS. 4a and 4b show one embodiment of a top case portion for a cassette or cartridge including fluid control features.

DETAILED DESCRIPTION

Figure 1:
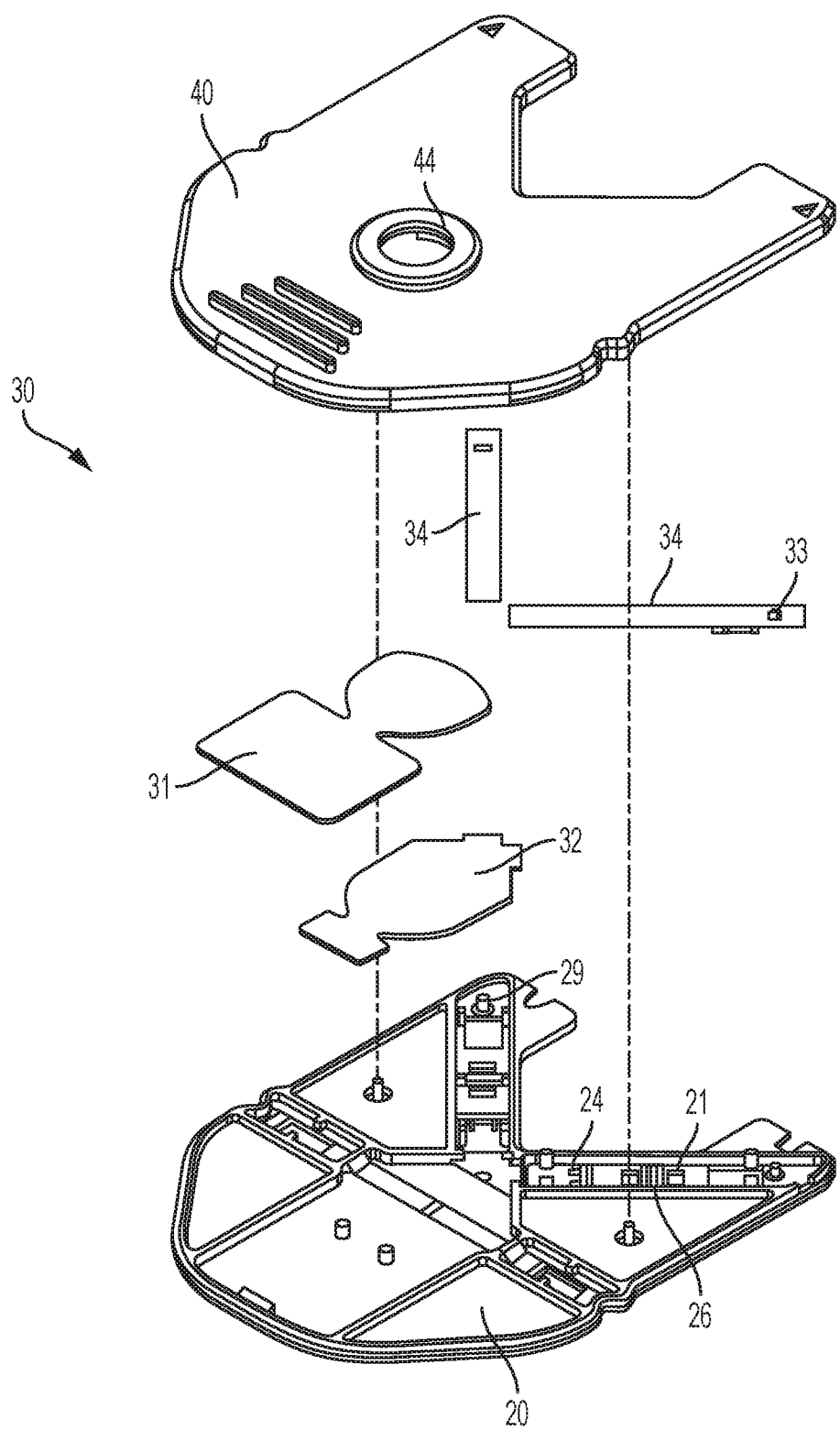
FIG. 1 shows one embodiment of a generalized cassette or cartridge including fluid control features.

Certain terminology is used herein for convenience only and is not to be taken as a limitation on the embodiments of the systems and methods for controlling excessive fluid flow in a cassette designed to receive a fluid sample. In the drawings, the same reference letters are employed for designating the same elements throughout the several figures. In some embodiments, systems and methods for controlling excessive fluid flow in a cassette designed to receive a fluid sample include a specially designed dam feature to prevent the backsplash of blood.

As seen in FIG. 1, a disposable cartridge 30 is provided. Cartridge 30 has a top 40 and a bottom 20, which are placed together such that they sandwich a sample pad 32 and two lateral flow assay test strips 34 therebetween. It is to be understood that the design of cartridge 30 is merely exemplary. Thus, additional designs including systems with only one, or more than two, test strips 34 therein can be used by slightly modifying this cartridge design.

In operation, a fluid sample is introduced into cartridge 30 through a sample receiving top hole 44 in top 40. The fluid sample may be a drop of blood, but is not so limited. The top hole 33 may be designed and shaped to receive a sampler. The sampler is typically used in applications that utilize a premix step. One such sampler is referred to as a redwood sampler. The sample is first received onto a sample receiving pad 32. From there, the fluid sample wicks onto test strips 34. A chemical reaction then occurs within each of test strips 34, which may be detected optically by a meter (not shown) through optical interrogation apertures 21 in bottom 20. In preferred embodiments, test strips 34 are lateral flow assay test strips, and the reaction that occurs thereon is measured by an optical system (e.g., reflectometers) in the meter.

Fluid control features may assist in controlling fluid movement both (a) from sample receiving pad 32 onto test strips 34 and (b) through test strips 34. These fluid control features, and their respective advantages, will be described fully below.

Figure 2:
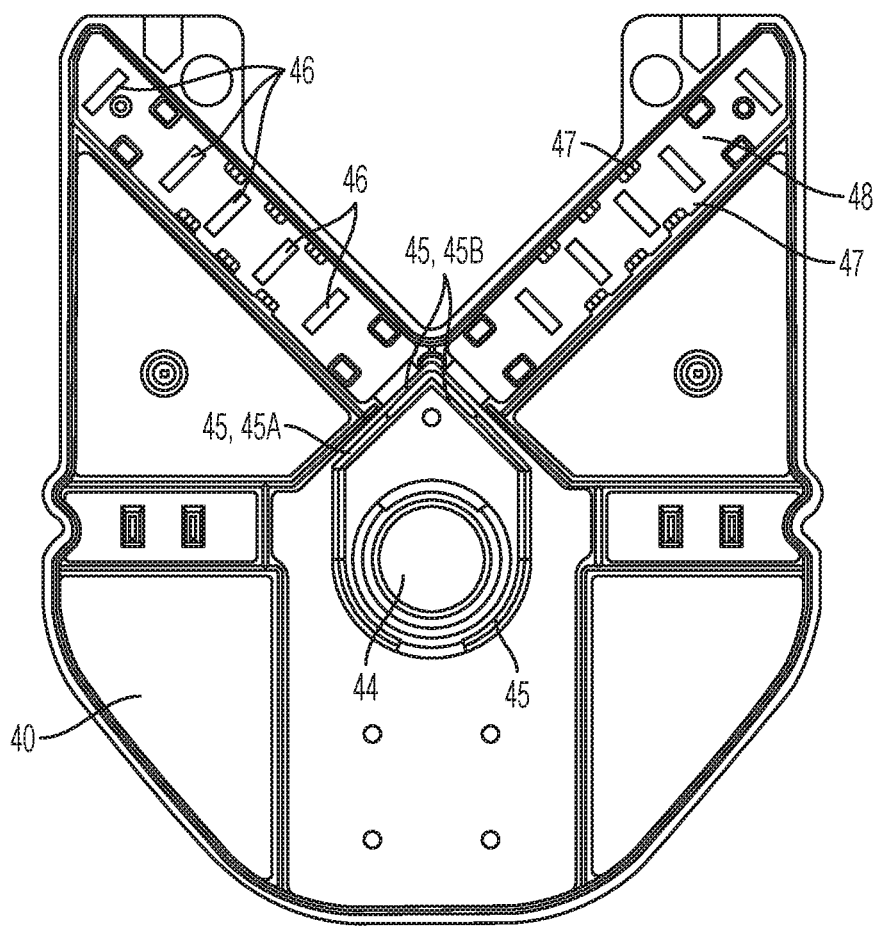
FIG. 2 shows one embodiment of a top case portion for a cassette or cartridge including fluid control features.

FIG. 2 shows further details of top 40, as follows. As stated above, top 40 has a hole 44 through which a fluid sample is introduced. A pinch wall 45 extends downward from top 40, having a first portion 45A and a second portion 45B. Pinch wall 45 is positioned to sit directly on top of sample receiving pad 32. Additionally, absorbent pad 31 is provided to absorb excess fluid and control the flow of fluid. First portion 45A extends downward a greater distance from top 40 than second portion 45B extends downward from top 40 (i.e., pinch wall portion 45A has a greater height than pinch wall portion 45B). As a result, when top 40 and bottom 20 are placed together, first portion 45A compresses sample pad 32 more than second portion 45B compresses sample pad 32. Together, portions 45A and 45B may comprise a continuous wall around hole 44, as shown. As will be explained with reference to FIG. 4 below, this feature is used to advantageously control fluid flow movement from sample pad 32 onto test strips 34.

In accordance with the illustrated embodiments, the pinch wall is positioned on top of the sample pad. However, the present invention is not so limited. For example, it is to be understood that the pinch wall may, instead, be positioned below the sample pad. Alternatively, systems where pinch walls are positioned both above and below the sample pad are contemplated within the scope of the present invention.

In addition, top 40 further includes a plurality of downward projecting support ribs 46. Support ribs 46 are positioned on top of test strips 34 when top 40 and bottom 20 are placed together. Support ribs 46 extend transversely across test strips 34. Support ribs 46 are used to assist in advantageously controlling fluid flow through test strips 34.

As can be seen, support ribs 46 preferably may be in the form of pedestals (i.e., the side edges of support ribs 46 do not contact the side edges 47 of chamber 48). In one exemplary embodiment, the width of support ribs 46 does not exceed the width of test strips 34. Thus, transverse support ribs 46 do not extend beyond the sides of test strips 34. Pinch wall 45A projects farther downward from top 40 than does pinch wall 45B. As a result, pinch wall 45A compresses sample pad 32 to a greater degree than pinch wall 45B. In one exemplary embodiment, pinch wall 45A compresses 60% to 90% of the height of sample receiving pad 32, and pinch wall 45B compresses 2% to 30% of the height of the sample receiving pad. In particular embodiments, pinch wall 45A compresses 70% to 80% of the height of sample receiving pad 32, and pinch wall 45B compresses 5% to 15% of the height of the sample receiving pad. It is to be understood that the above compression ranges are merely exemplary, and the exact compression ranges will depend upon the compressibility of the sample pad material, with more porous or open materials requiring higher compression. In some configurations, the compression may vary based on whether the sample is introduced from the bottom or the top of the system.

As a result, fluid received into sample pad 32 (at portion 32A) has an easier time flowing under the bottom of pinch wall portion 45B (as opposed to flowing under pinch wall portion 45A). Therefore, when a drop initially reaches sample pad portion 32A (or when several drops fill or partially fill the chamber), the fluid will first pass under pinch wall 45B into sample pad portion 32 (i.e., the portion adjacent to test strip 34). From there, the fluid sample will wick into test strip 34. However, the speed of fluid movement is controlled by the presence of pinch wall 45. Specifically, the presence of pinch wall 45 will advantageously prevent the fluid sample from simply flooding uncontrollably onto test strip 34, or otherwise splashing or leaking around in the interior of cartridge 30.

Figure 3:
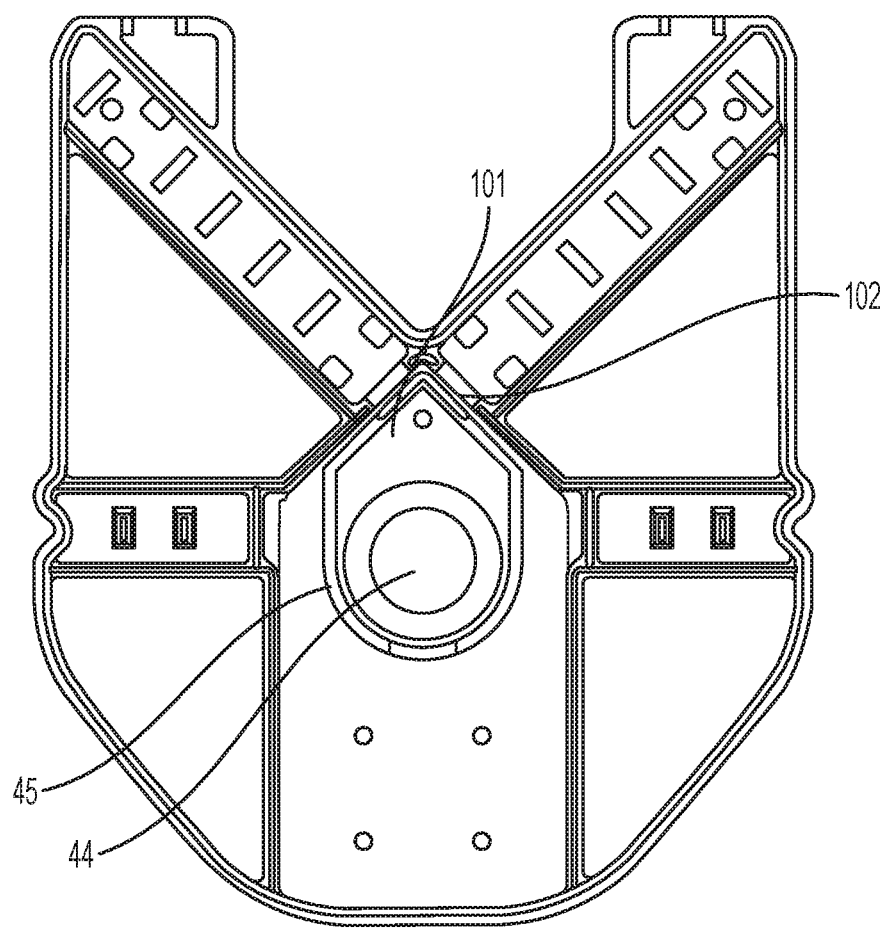
FIG. 3 shows one embodiment of a top case portion for a cassette or cartridge including fluid control features.

Additionally, in some embodiments, it has been discovered that sample backflow may occur after application of the sample through hole 44. FIG. 3 shows one embodiment of a cassette or cartridge top that includes hole 44 and pinch wall 45. Fluid in area 101 may backflow toward hole 44 instead of toward the interface 102 with test strips 34. In some scenarios, this backflow may hinder proper absorption of the sample into test strips 34. This may be a detriment to the proper timing of the test strip and test functions.

FIGS. 4a and 4b show an additional embodiment of a system for controlling excessive fluid flow in a cassette. In this embodiment, a dam 110 is included to prevent backflow. This dam, arranged in the cover, sits on top of the sample pad 32 and prevents the backflow of excessive fluid that pools on the other side of the dam 110. This improves the function and timing of the system.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each attachment may be interchanged between embodiments.

What is claimed as new and desired to be protected by Letters Patent of the United States is:

1. A pinch wall and dam system for controlling fluid flow movement between a sample receiving pad and a test strip, comprising:
   a sample receiving pad, having a top surface, the top surface facing upwards;
   a test strip in contact with the sample receiving pad;
   a pinch wall sitting on top of the sample receiving pad on the top surface, the pinch wall compressing the sample receiving pad, the pinch wall comprising: a first portion separating a sample receiving portion of the sample receiving pad from a portion of the sample receiving pad positioned adjacent to the test strip, and a second portion separating the sample receiving portion of the sample receiving pad from a portion of the sample receiving pad positioned away from the test strip, wherein the portion of the sample receiving pad that receives the sample thereon is positioned on an opposite side of the pinch wall from the portion of the sample receiving pad positioned away from the test strip, wherein the first portion of the pinch wall compresses the sample receiving pad to a lesser degree than the second portion of the pinch wall, wherein fluid seeps more quickly under the first portion of the pinch wall than under the second portion of the pinch wall, such that the test strip becomes saturated prior to excess fluid being absorbed in the portion of the sample receiving pad away from the test strip such that the test strip does not become flooded, the portion of the sample receiving pad positioned away from the test strip being sufficiently sized to absorb the excess fluid; and
   a dam, sitting on top of the sample receiving pad, the dam preventing the backflow of fluid from an area near the first portion of the pinch wall.

2. The system of claim 1, wherein the first and second portions of the pinch wall together continuously surround the sample receiving portion of the sample receiving pad.

3. The system of claim 1, wherein the pinch wall compresses the sample receiving pad such that fluid received onto the sample receiving pad preferentially tends to flow from the sample receiving portion of the sample receiving pad into the portion of the sample receiving pad positioned adjacent to the test strip, and less so from the sample receiving portion of the sample receiving pad to the portion of the sample receiving pad positioned away from the test strip.

4. The system of claim 1, wherein the sample receiving pad is in a case with a cartridge with a top portion and a bottom portion, and wherein the pinch wall and dam protrude from the top portion.

5. The system of claim 1, wherein the dam compresses the receiving pad.

6. The system of claim 1, wherein the dam does not significantly compress the receiving pad, but forms a barrier against backflow.

7. The system of claim 4, wherein the top portion includes a hole for receiving a sample, wherein the dam is oriented on an edge of the hole.

8. The system of claim 7, wherein the edge of the hole is a portion of the hole proximate to the first portion of the pinch wall.

9. A method of controlling fluid flow movement between a sample receiving pad and a test strip, comprising:
   providing a pinch wall and dam system, the system comprising:
      a sample receiving pad, having a top surface, the top surface facing upwards;
      a test strip in contact with the sample receiving pad; and
      a pinch wall sitting on top of the sample receiving pad on the top surface, the pinch wall compressing the sample receiving pad, the pinch wall comprising: a first portion separating a sample receiving portion of the sample receiving pad from a portion of the sample receiving pad positioned adjacent to the test strip, and a second portion separating the sample receiving portion of the sample receiving pad from a portion of the sample receiving pad positioned away from the test strip, wherein the portion of the sample receiving pad that receives the sample thereon is positioned on an opposite side of the pinch wall from the portion of the sample receiving pad positioned away from the test strip, wherein the first portion of the pinch wall compresses the sample receiving pad to a lesser degree than the second portion of the pinch wall, wherein fluid seeps more quickly under the first portion of the pinch wall than under the second portion of the pinch wall, such that the test strip becomes saturated prior to excess fluid being absorbed in the portion of the sample receiving pad away from the test strip such that the test strip does not become flooded, the portion of the sample receiving pad positioned away from the test strip being sufficiently sized to absorb the excess fluid;
      a dam, sitting on top of the sample receiving pad, the dam preventing the backflow of fluid from an area near the first portion of the pinch wall;
   placing a sample on the sample receiving pad;
   flowing the sample to the test strip via the first portion of the pinch wall; and
   preventing backflow of the sample with the dam.

10. The method of claim 9, wherein the first and second portions of the pinch wall together continuously surround the sample receiving portion of the sample receiving pad.

11. The method of claim 9, wherein the pinch wall compresses the sample receiving pad such that fluid received onto the sample receiving pad preferentially tends to flow from the sample receiving portion of the sample receiving pad into the portion of the sample receiving pad positioned adjacent to the test strip, and less so from the sample receiving portion of the sample receiving pad to the portion of the sample receiving pad positioned away from the test strip.

12. The method of claim 9, wherein the sample receiving pad is in a case with a cartridge with a top portion and a bottom portion, and wherein the pinch wall and dam protrude from the top portion.

13. The method of claim 9, wherein the dam compresses the receiving pad.

14. The method of claim 9, wherein the dam does not significantly compress the receiving pad, but forms a barrier against backflow.

15. The method of claim 9, wherein the top portion includes a hole for receiving a sample, wherein the dam is oriented on an edge of the hole.

16. The method of claim 9, wherein the edge of the hole is a portion of the hole proximate to the first portion of the pinch wall.

* * * * *